United States Patent
Kvassnes et al.

(10) Patent No.: US 11,054,353 B2
(45) Date of Patent: Jul. 6, 2021

(54) BOND STRENGTH TESTING

(71) Applicant: RESTONE AS, Fyllingsdalen (NO)

(72) Inventors: Astri Kvassnes, Hjellestad (NO); Jill Angelique Clausen, Fyllingsdalen (NO); Benny Suryanto, Edinburgh (GB); Jaehwan Kim, Goyang-si (KR)

(73) Assignee: RESTONE AS, Fyllingsdalen (NO)

( * ) Notice: Subject to any disclaimer, the term of this patent is extended or adjusted under 35 U.S.C. 154(b) by 0 days.

(21) Appl. No.: 17/103,261

(22) Filed: Nov. 24, 2020

(65) Prior Publication Data

US 2021/0164875 A1 Jun. 3, 2021

(51) Int. Cl.
*G01N 3/62* (2006.01)
*G01N 1/28* (2006.01)
*G01N 33/38* (2006.01)
*G01N 3/24* (2006.01)

(52) U.S. Cl.
CPC .............. *G01N 3/62* (2013.01); *G01N 1/286* (2013.01); *G01N 3/24* (2013.01); *G01N 33/383* (2013.01); *G01N 2203/0025* (2013.01)

(58) Field of Classification Search
CPC ........... G01N 3/62; G01N 1/286; G01N 3/24; G01N 33/383; G01N 2203/0025; G01R 31/2893; B01L 3/50825; B01L 3/502

USPC ............................................ 73/841
See application file for complete search history.

(56) References Cited

U.S. PATENT DOCUMENTS

| | | | | |
|---|---|---|---|---|
| 3,406,567 A | * | 10/1968 | Terry | G01N 3/24 73/841 |
| 8,794,078 B2 | * | 8/2014 | Darbe | G01N 3/10 73/803 |
| 9,352,314 B2 | * | 5/2016 | Vemalarajah | B01L 3/5023 |
| 9,414,813 B2 | * | 8/2016 | Engel | A61B 10/0051 |

* cited by examiner

*Primary Examiner* — Octavia Hollington
(74) *Attorney, Agent, or Firm* — Flener IP & Business Law; Zareefa B. Flener

(57) ABSTRACT

The invention pertains to performing bonding strength testing between a test material and a container. A sample preparation device to make a test sample was disclosed. This device included a container with an insert on each end. The inserts have a portion that protrudes into the container. When test material is added to the sample preparation device, a groove was formed in test sample. These grooves reduce the amount of boundary effects that are present during testing. A system and method for performing bond strength testing was also disclosed. In this system, a test sample was formed using the sample preparation device. This is placed upon a support and a half-spherical force applier is placed on top of the test sample. A press is used to apply force to the force applier and indirectly to the test sample.

25 Claims, 8 Drawing Sheets

BOND STRENGTH TESTING

CROSS REFERENCE TO RELATED APPLICATIONS

Figure 1:
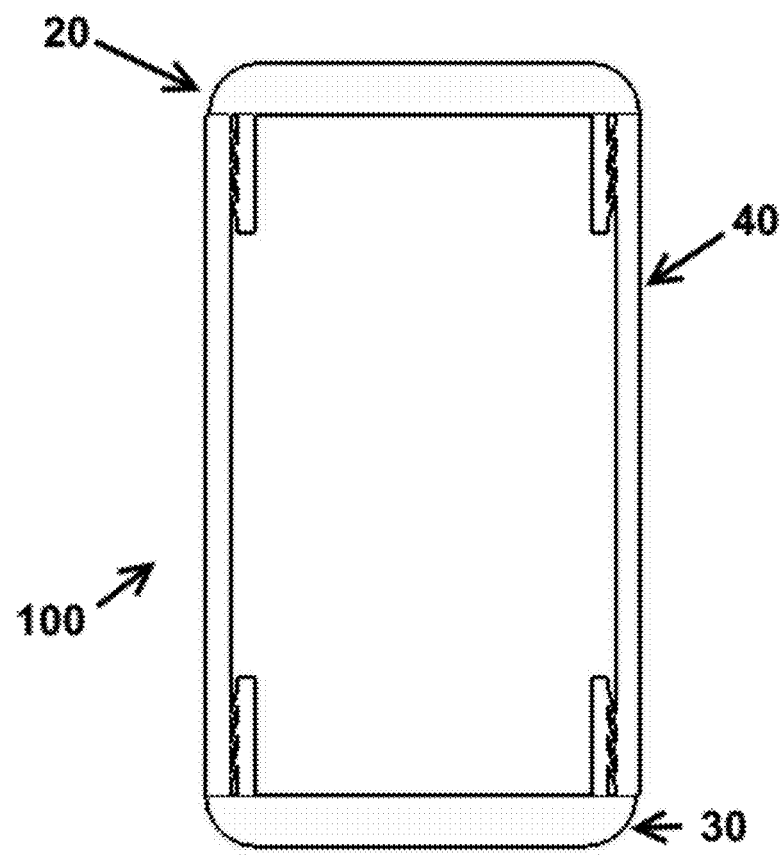

This application claims priority to a pending Norwegian application No. NO20191422 (filed Dec. 2, 2019). The entire contentions of which are hereby incorporated by reference.

FIELD OF THE INVENTION

The present invention relates to a bond strength sample preparation device. The present invention also relates to a hardened sample formed from curing the sample material inside of the sample preparation device. The present invention further relates to a sample testing system. Lastly, the present invention also relates to a method of testing bond strength between a hardened sample and a container.

BACKGROUND

This invention is focused upon the testing of cement in industrial applications where the bond strength between a material (often steel) and cementitious materials (often cement paste, cement mortar and/or concrete). Cement mortar generally contains inclusions (often fine aggregates <4 mm maximum size) whereas concrete contains inclusions (often coarser aggregates or rocks with a maximum size of 20 mm). This invention is particularly well suited for the oil and gas industry.

Cement is an important component in the oil and gas industry. Within a well, it is used in several phases of operation (e.g. completion and abandonment). One of the most important applications of cement is to support the well casing. It is important to be able to give accurate and realistic tests of the properties of the cement before the cement is actually used on site.

There are three different kinds of bond strengths that are considered important for the application of cement to achieve a desired result: shear bond strength, hydraulic bond strength, and tensile bond strength. Even though hydraulic bond strength and tensile bond strength between cement and another surface are important, it is the testing of shear bond strength that is the focus for this invention.

The shear bond strength gives an idea on how good the interfacial bond between the casing and the cement under a relative displacement. The shear bond strength is defined as the ratio of the total force to the total contact area required to initiate relative movement between two materials. This is usually tested in a Loading Frame which uses hydraulics to apply a load upon test sample that is arranged vertically within the device. There is a large degree of freedoms when choosing the dimensions of a test sample as long as it can fit within the apparatus.

It is very important that a scientist or engineer can scale up from the small-scale material tests of different bonding strengths to the full scale application. This will allow a company to decide upon the cement properties that are needed and decide which cement will function best at the specific conditions. Influencing factors are, for example, the size of the test sample, curing conditions, pipe dimensions and the quality finish on the pipe surface.

A goal of the sample preparation for small scale tests is to provide as accurate of a measurement of the interfacial shear bond strength as possible. Additionally, it is important that samples can be produced quickly and with the same properties. On one side, it is a simple matter to make sure that the quest equipment itself is calibrated correctly and has the required sensitivity. However, it is not such an easy matter to ensure that the bond strength tests are indeed testing the bond strength alone. Other factors can include friction between the test equipment and the cement and the properties of the cement sample itself. Another important factor is misalignment of the application of force between the cement plug and the downwards applied force as it can increase local bond stresses and hence lead to a premature failure. Calibrating the exact alignment of the force to the sample is a time consuming process and often needs to be repeated several times.

Of particular importance is the properties of the cement sample at the ends that are referred to as "boundary effects". These effects are mostly seen at the top and bottom portions of the sample. At both ends, it is common for the cement to cure in a different manner than the main body of the sample and this is generally due to problems occurring after casting such as material segregation (i.e. the movement of cement particles downward) and bleeding (i.e. the movement of mixing water upward thereby creating a weak cement layer on top). These phenomena will result in a different bond strength between the cement sample and the metal pipe at the ends. This results in an incorrect measurement of the bond strength.

Ignoring these boundary effects will result in bond strength measurements that are not accurate and suffer from size effect. Common techniques to overcome this is by grinding the ends of cement in the sample before use. This can be a time consuming process that adds both delay and extra costs to the testing process. Note that it is even harder to get accurate data on the bond strength as a function of temperature for samples that were taken out of an oven and are not inserted into the quest equipment quickly.

Another technique for removing boundary effects is to simply take multiple measurements and attempt to remove it using mathematical methods. This adds complexity to the problem and is often very sensitive to the edge effect model that is being used.

Further information of previous shear bond strength testing can be found in CN107044939, US2014174192A1, and WO2010094925.

Unless specified otherwise, by "bonding strength" (or linguistic variations thereof) it is meant the shear bond strength.

OBJECTS AND ADVANTAGES OF THE PRESENT INVENTION

The present invention solves the problems discussed above as well as others that will be apparent to one skilled in the art. One skilled in the art will also understand that there are other advantages and applications of the present invention.

The sample that is produced with the present invention has reduced boundary effects when compared to other sample preparation methods. Part of this is accomplished with inserts that have a protrusion that extends into the test container during the curing process. These protrusions prevent the cement from binding at the ends of the pipe and therefore minimize boundary effects. Another advantage of the use of the insert is to produce a flat surface that would facilitate uniform application of stresses.

One advantage of the present invention is that it is much easier than previous solutions to make a batch of test samples that exhibit the same physical characteristics.

Another advantage of the invention is that it is easy to align force correctly from the load frame with the test sample without need for numerous recalibrations of the angle of applied force. Part of this is accomplished by using an adapter between the force source and the test sample which has the ability to self-calibrate the force.

The present invention will produce test samples that can quickly be made and inserted into bond strength test equipment with an acceptable level of loss of temperature.

SUMMARY OF THE INVENTION

In a first aspect, the present invention relates to a shear bond strength sample preparation device described by including:
- a container including a container inside a tested container end and an untested container end;
- an untested insert including an untested insert body with an untested insert protrusion extending from the untested insert body wherein an untested insert surface is arranged on the untested insert body between the untested insert body and the untested insert protrusion;
- a tested insert including a tested insert body with a tested insert protrusion extending from the tested insert body wherein an tested insert surface is arranged on the tested insert body between the tested insert body and the tested insert protrusion;
- wherein:
- the untested insert is arranged such that the untested insert protrusion is within the container of the untested container end;
- the tested insert is arranged such that the tested insert protrusion is within the container on the tested container end.
- the untested insert protrusion is arranged on the untested insert body such that the untested insert protrusion is directly or indirectly in contact with the container inside; and
- the tested insert protrusion is arranged on the tested insert body such that the tested insert protrusion is directly or indirectly in contact with the container inside.

In embodiment of the first aspect, the tested insert surface is substantially flat.

In an embodiment of the first aspect, the tested insert protrusion and/or untested insert protrusion extends far enough to remove boundary effects, preferably at a distance of between 10 and 30 percent, preferably between 15 and 25 percent, and most preferably between 15 and 20 percent of the height of the container.

In an embodiment of the first aspect, the container has a height of between 25 and 500 mm, preferably between 30 and 300 mm, and most preferably 30 mm.

In an embodiment of the first aspect, the container has an inner diameter of at least five times the maximum size of the particulate materials within the test sample.

In an embodiment of the first aspect, the untested insert and/or the tested insert is formed of one or more of the following materials: plastic, rubber, and silicone.

In an embodiment of the first aspect, the tested insert is arranged such that there is a water-tight seal between the tested insert the container inside.

In an embodiment of the first aspect, the tested insert is arranged to shear where the tested body is in contact with the container In embodiment of the first aspect, a sealer to improve waterproofing between the tested insert protrusion and the container inside.

In an embodiment of the first aspect, the sealer comprises one or more of the following materials: heat resistant silicone sealant, rubber (i.e. 0 ring), and semi solid lubricant.

In an embodiment of the first aspect, the container includes one of more of the following materials of: steel, iron, cored stone, and cementitious materials, preferably steel and cored stone, most preferably steel.

In an embodiment of the first aspect, the container is a pipe.

In a second aspect, the present invention relates to a shear bond strength hardened sample described by including:
  i. an untested sample end on one end of the hardened sample, including:
    1. an untested groove shaped in a complimentary manner of the untested insert protrusion within the sample material;
  ii. a tested sample end on an opposite end of the hardened sample as the untested sample end, including:
    1. an tested groove shaped in a complimentary manner of the tested insert protrusion within the sample material;
    2. a tested surface shaped in a complementary manner to the tested insert surface, preferably flat; and
  iii. an outer sample surface with a cross sectional shape equal to that of the container inside.

In an embodiment of the second aspect, the sample material is cement paste, cement mortar, and/or concrete, preferably cement paste and/or cement mortar, most preferably cement paste and mortar.

In a third aspect, the present invention relates to a shear bond strength sample testing system described by including:
  a test sample including:
    the container according to the first aspect or any embodiments thereof;
    the hardened sample according to the second aspect or any embodiments thereof arranged such that the hardened sample is bonded to the container inside;
  a support arranged such that the container is held in a fixed position during testing;
  a force applier including a force contact surface
  a displacement force source;
  wherein:
    the support keeps the container from moving during testing;
    the force contact surface is in at least partial contact with the tested surface at an applied force surface; and
    the displacement force source applies a displacement force to an applied force surface in a direction at least partially from the tested container end toward the untested container end.

In an embodiment of the third aspect, the system further includes an force adapter arranged between the force applier and the hardened sample; wherein
  i. the force adapter includes an adapter displacement surface on one end a force adapter contact surface on the other; and
  ii. the adapter displacement surface is in at least partial contact with the force contact surface and the adapter contact surface is in at least partial contact with the tested surface at the applied force surface.

In an embodiment of the third aspect, the applied force surface has the same cross sectional shape as the container inside, preferably that of an ellipse, and is arranged such that it fits inside of the container during testing.

In an embodiment of the third aspect, the force applier wherein the displacement contact surface is shaped as a portion of an ellipsoid, preferably spherical.

In an embodiment of the third aspect, the force applier is constructed of a material including one or more of the following: stainless steel, carbon steel, and duplex steel, preferably stainless steel and duplex steel, most preferably stainless steel.

In an embodiment of the third aspect, the support has a support base arranged such that the untested container end rests upon the support base.

In an embodiment of the third aspect, the support has a base groove and arranged such that the untested container end rests at least partially within the support groove.

In an embodiment of the third aspect, the base support has a support opening arranged such that the hardened sample does not make contact with the support, during the test.

In an embodiment of the third aspect, the support opening is circular and as at least as large as the diameter of the untested sample end.

In an embodiment of the third aspect, there is a tested insert arranged to shear where the tested body is in contact with the tested container end upon application of displacement force upon the tested insert.

In an embodiment of the third aspect, there is a container insulator to provide thermal insulation, wherein the container is arranged inside of the container insulator In a fourth aspect, the present invention relates method of testing shear bond strength of a test sample in a shear bond strength same testing system described by including the following steps:
a) arranging the tested insert into the tested container end of the container;
b) providing sample material to the container through the untested container end to a height such that the untested insert protrusion is at least partially covered by performing one of the following steps:
  i. providing a desired amount of sample material to the container and then arranging the untested insert into the untested container end; optionally providing a further amount of sample material through an opening in the untested insert;
  ii. arranging the untested insert into the untested container end and then providing a desired amount of sample material to the container through an opening in the untested insert;
c) waiting until the sample material cures into a hardened sample;
d) removing the tested insert and untested insert; prior to
e) arranging the container in the support such that the container is held in place during the test;
f) arranging the force applier between the displacement force source and the tested sample end such that the displacement contact surface is in at least partial contact with the tested surface; and
g) applying displacing force upon the hardened sample at the applied force surface between the tested surface and the displacement contact surface; and thereby
h) causing the hardened sample to displace within the container in the direction of the applied force.

In an embodiment of the fourth aspect, where step (f) includes:
a force adapter including a force adapter displacement surface is arranged at one end and a force adapter contact surface is arranged at the other;
the force adapter is arranged between the force applier and the tested sample end such that the force adapter displacement surface is in at least partial contact with the displacement contact surface and the force adapter contact surface is in at least partial contact with the tested surface and in step (g):
the applied force surface is between the tested surface and the force adapter contact surface instead of between displacement contact surface and the tested surface.

In an embodiment of the fourth aspect, the tested insert protrusion and/or untested insert protrusion extends into the sample material far enough to remove boundary effects, preferably at a distance of between 10 and 30 percent, preferably between 15 and 25 percent, and most preferably between 15 and 20 percent of the height of the container

A CONDENSED SUMMARY OF THE INVENTION

The invention pertains to performing bonding strength testing between a test material and a container. A sample preparation device to make a test sample will be disclosed. This device includes a container with an insert on each end. The inserts have a portion that protrudes into the container. When test material is added to the sample preparation device, a groove is formed in test sample. These grooves reduce the amount of boundary effects that are present during testing.

A system and method for performing bond strength testing will also disclosed. In this system, a test sample is formed using the sample preparation device. This is placed upon a support and a half-spherical force applier is placed on top of the test sample. A press is used to apply force to the force applier and indirectly to the test sample.

DESCRIPTION OF THE DIAGRAMS

Figure 2:
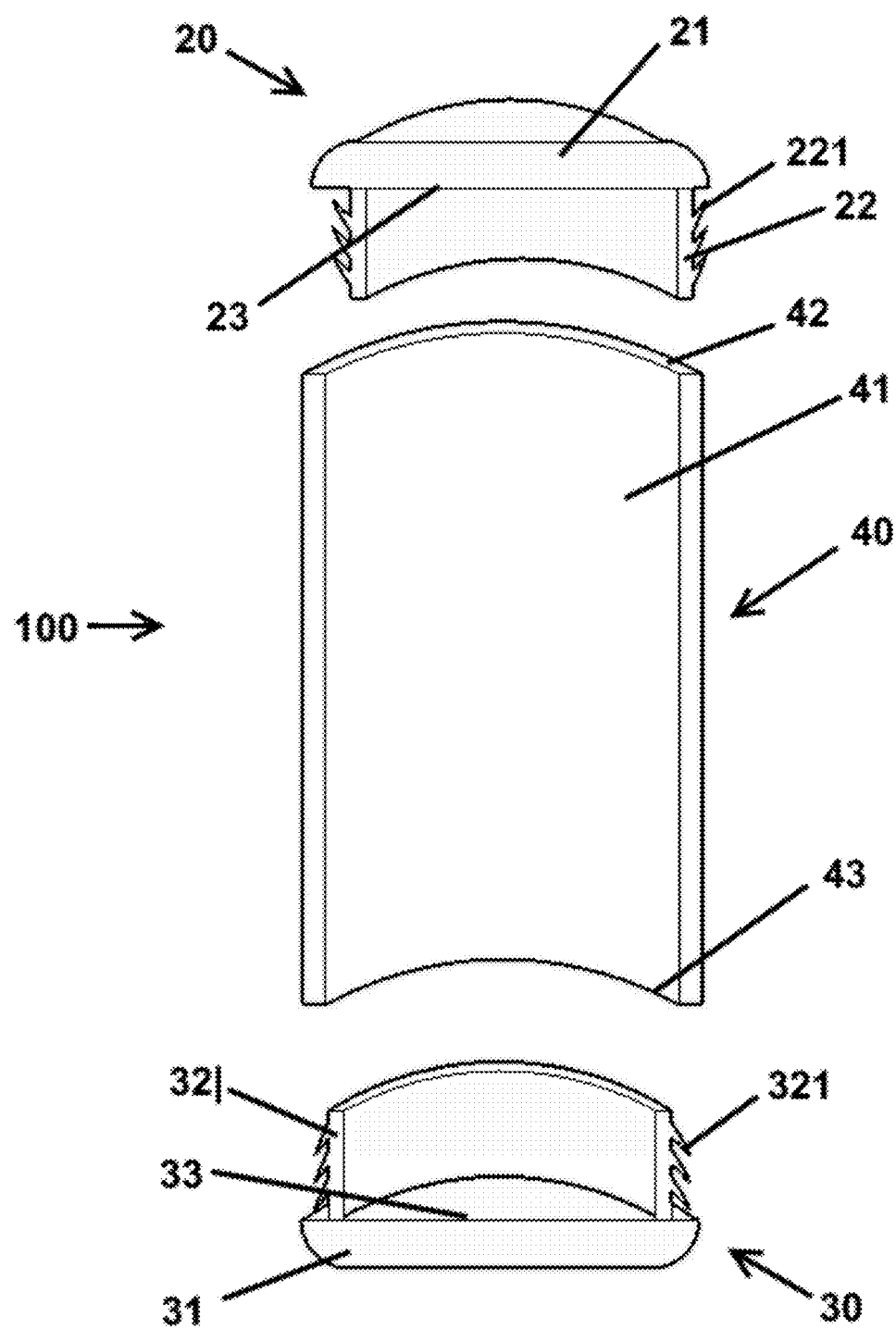
Figure 3A:
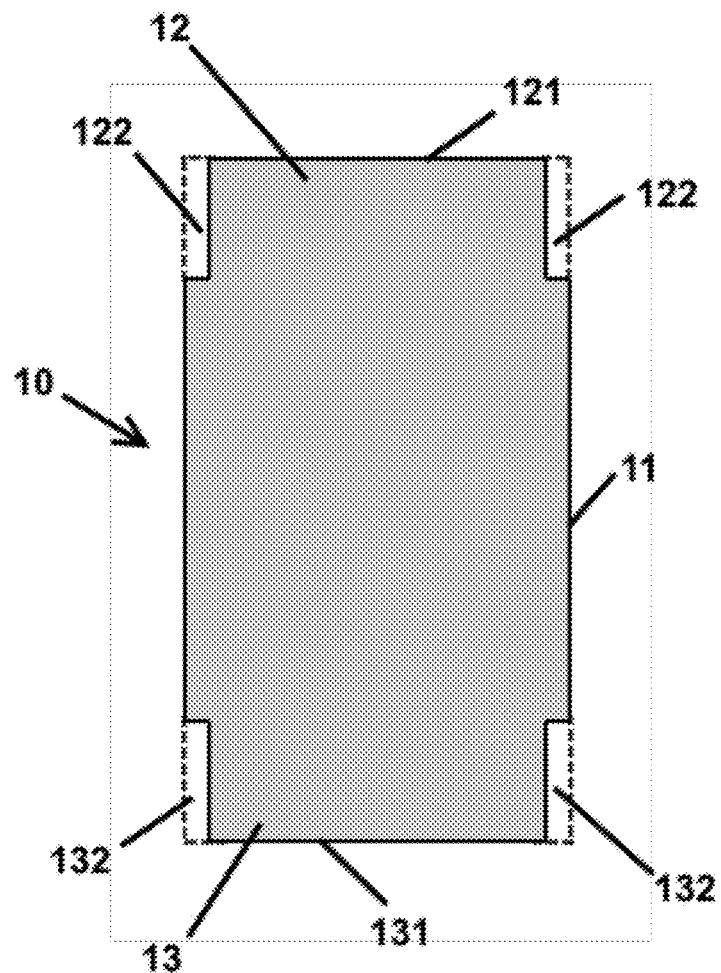
Figure 3B:
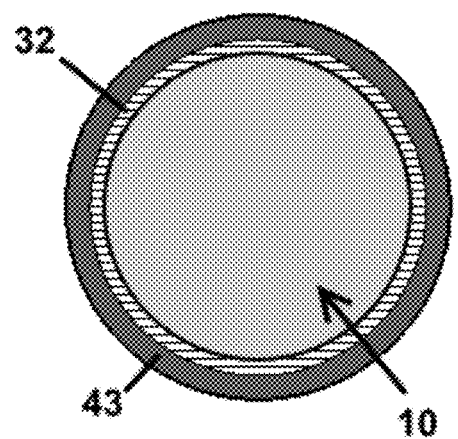
Figure 3C:
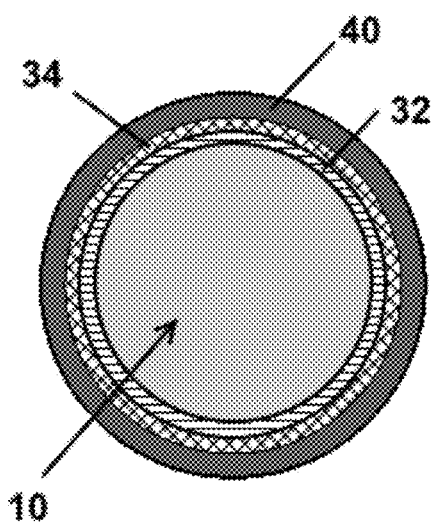
Figure 3D:
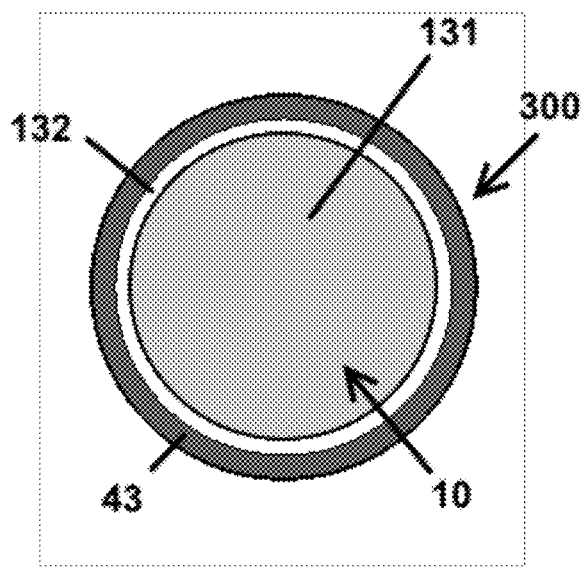

The above and further features of the invention are a set forth with particularity in the appended claims and together with advantages thereof will become clearer from consideration of the following detailed description. Embodiments of the present invention will now be described, by way of example only, with reference to the following diagrams wherein:

FIG. 1 discloses an overview of the preferred device embodiment of the invention FIG. 2 discloses a longitudinal exploded perspective cross section of the preferred device embodiment of the invention FIG. 3A discloses a longitudinal cross sectional view of the hardened sample formed in the device FIG. 3B discloses a transverse cross sectional view of the preferred embodiment for preparation of the test sample in the device FIG. 3C discloses a transverse cross sectional view of an alternate embodiment for preparation of a test sample in the device FIG. 3D discloses a top view of the preferred embodiment of the test sample.

Figure 4A:
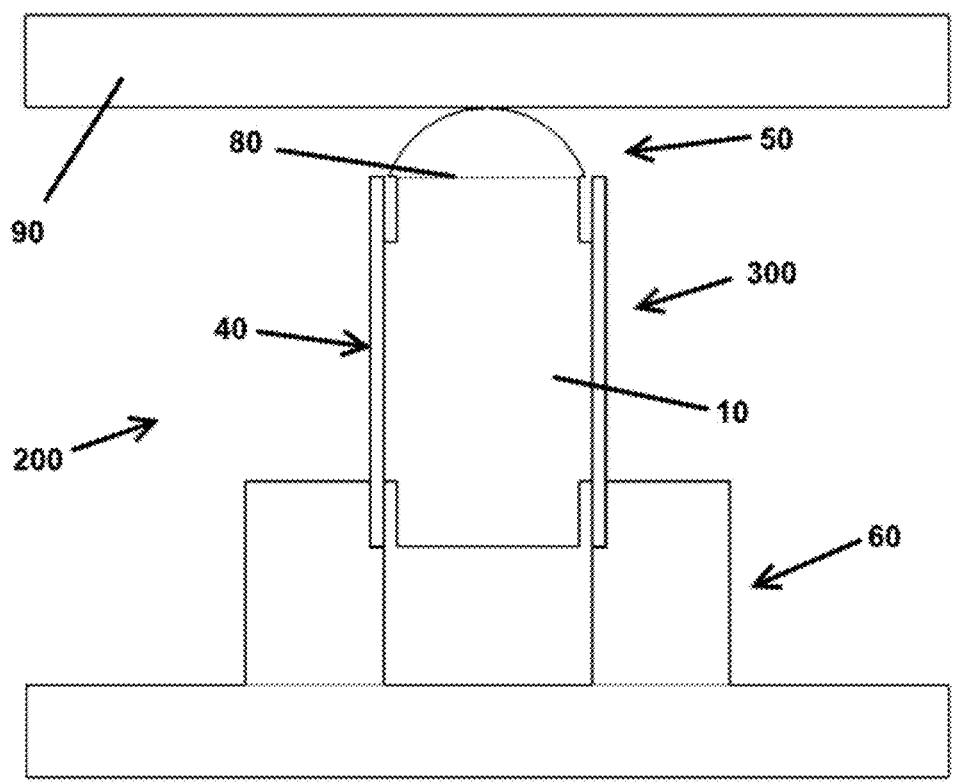

FIG. 4A discloses an overview of the preferred embodiment of the testing system

Figure 4B:
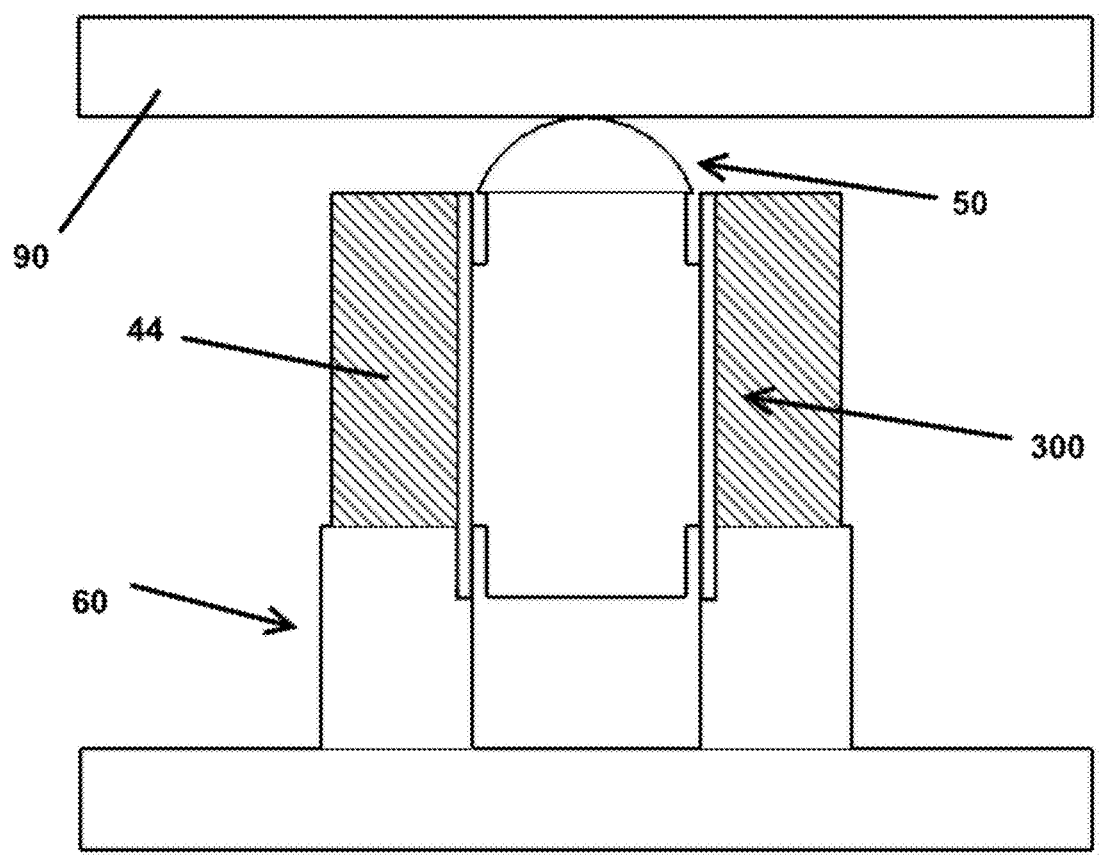

FIG. 4B discloses an overview of an alternative embodiment of the testing system with insulation.

Figure 5:
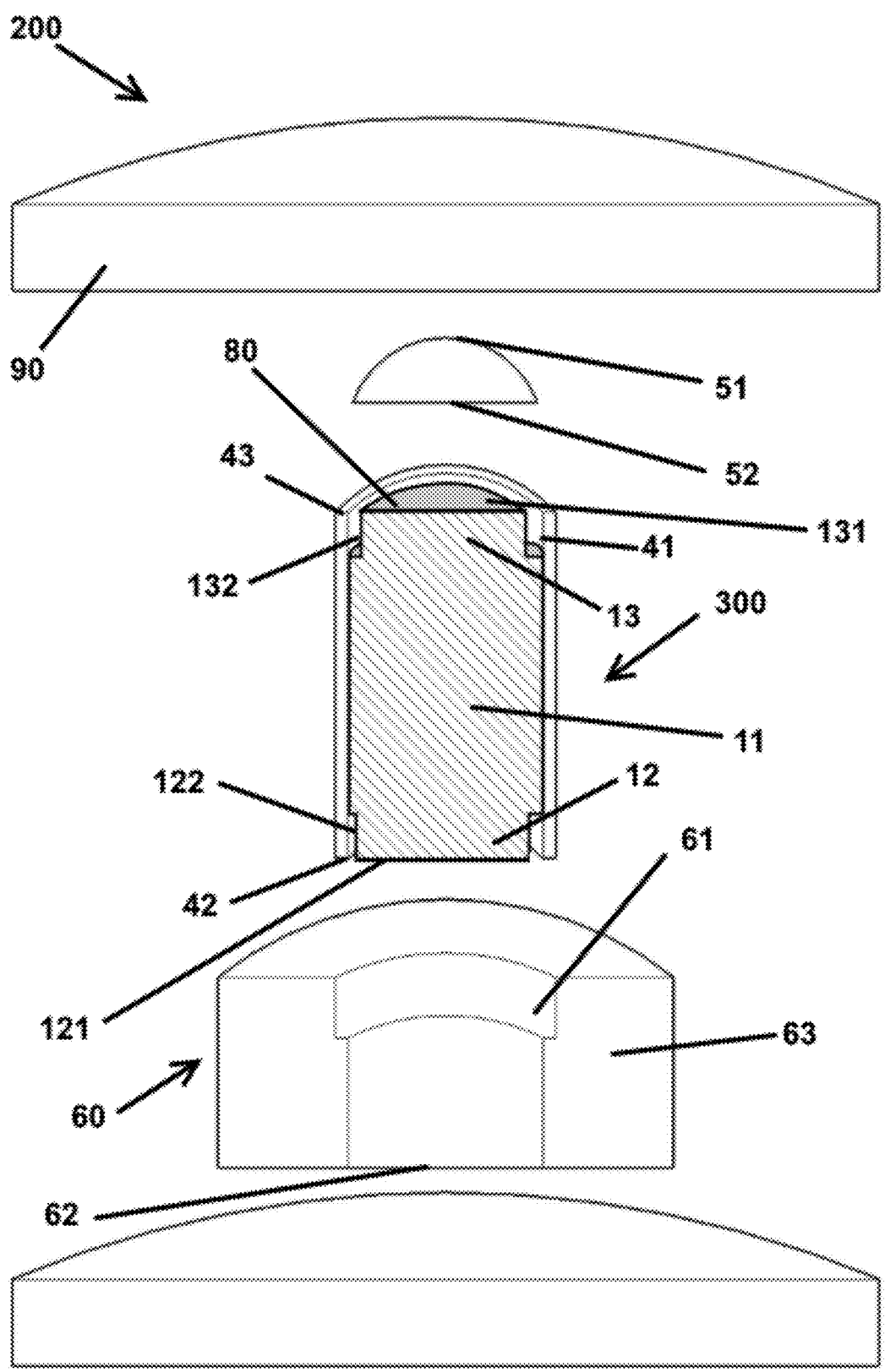
Figure 6:
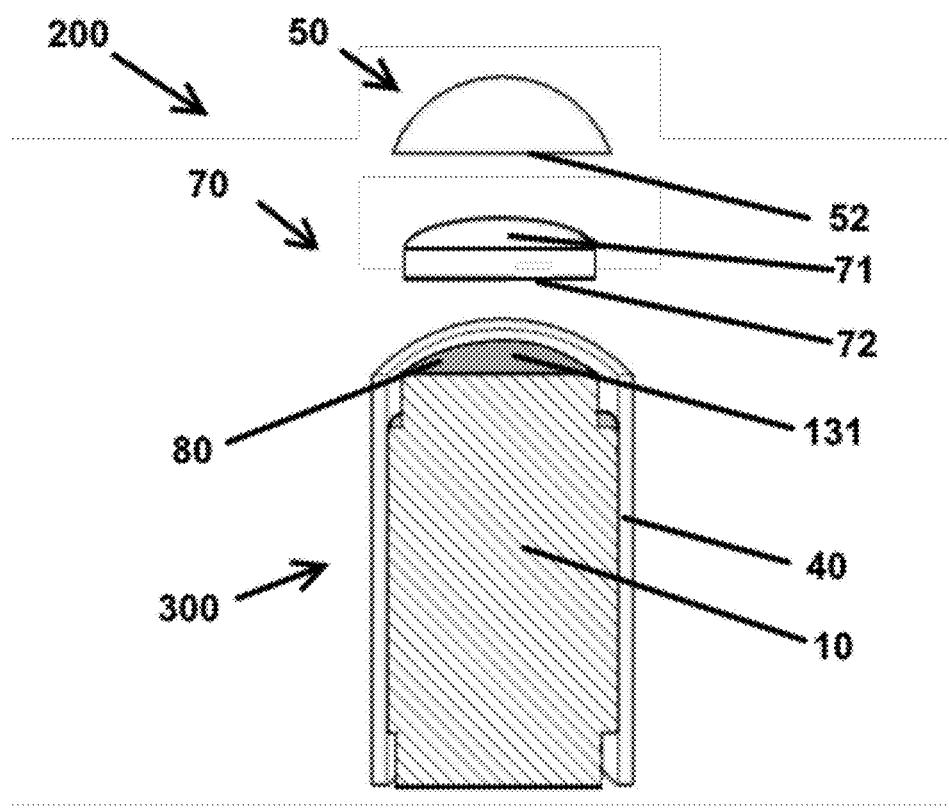

FIG. 5 discloses a longitudinal exploded perspective cross section of the preferred embodiment of the testing system FIG. 6 discloses a longitudinal exploded cross sectional view of an alternative embodiment of the testing system

LIST OF REFERENCE NUMBERS USED

| | |
|---|---|
| Sample Material | 1 |
| Hardened sample | 10 |
| Outer Sample Surface | 11 |
| Untested Sample End | 12 |
| Untested Surface | 121 |
| Untested Groove | 122 |
| Tested Sample End | 13 |
| Tested Surface | 131 |
| Tested Groove | 132 |
| Untested Insert | 20 |
| Untested Insert Body | 21 |
| Untested Insert Protrusion | 22 |
| Untested Insert Gripper | 221 |
| Untested Insert Surface | 23 |
| Tested Insert | 30 |
| Tested Insert Body | 31 |
| Tested Insert Protrusion | 32 |
| Tested Insert Gripper | 221 |
| Tested Insert Surface | 33 |
| Sealer | 34 |
| Container | 40 |
| Container Inside | 41 |
| Untested Container End | 42 |
| Tested Container End | 43 |
| Container Insulator | 44 |
| Force Applier | 50 |
| Displacement Force Surface | 51 |
| Force Contact Surface | 52 |
| Support | 60 |
| Support Base Groove | 61 |
| Support Base Opening | 62 |
| Support Base | 63 |
| Force Adapter | 70 |
| Force Adapter Displacement Surface | 71 |
| Force Adapter Contact Surface | 72 |
| Applied Force Surface | 80 |
| Displacement Force Source | 90 |
| Sample preparation device | 100 |
| Sample Testing System | 200 |
| Test Sample | 300 |

DESCRIPTION OF PREFERRED EMBODIMENTS OF THE INVENTION

Reference will now be made in detail to the present embodiments of the inventions, examples of which are illustrated in the accompanying drawings. Alternative embodiments will also be presented. The drawings are intended to be read in conjunction with both the summary, the detailed description, and an any preferred and/or particular embodiments, specifically discussed or otherwise disclosed. This invention may, however, be embodied in many different forms and should not be construed as limited to the embodiments set forth herein. These embodiments are provided by way of illustration only. Several further embodiments, or combinations of the presented embodiments, will be within the scope of one skilled in the art.

Direction terms such as up, down, left, right, above, below, etc. are being used in reference to the orientation of the elements in the figures. In no way is this intended as limiting.

As mentioned previously, testing of shear bond strength between a container and cement can be a difficult process.

The present invention is designed to simplify the preparation and testing of test samples. The follow is a rough summary of the invention. The test material (often cement) is added into a specialized sample preparation device. This device has inserts at the top and bottom, which has a portion that protrudes into the test material. These inserts creates a groove in the top and bottom of the test sample. These grooves remove the edges of the sample and thus reduces the boundary effects associated with hardening of a sample material inside of a container (often a steel pipe). This test sample comprising the container and the hardened sample material is then inverted, the inserts removed, and placed into a system that can apply a downwards force (often a hydraulic press) to test the bond strength between the hardened material and the container. By inverting the test sample prior to testing, a surface is presented to the force that is flat and absent of air bubbles. An element is placed on top of the test sample that better transfers the force to the test sample. Force is applied until the bond between the hardened sample material and the container breaks and the sample material begins to move.

The terms tested and untested sides, ends, and surfaces will be used. This is in reference to which portion of the test sample will be receiving the applied force during testing of the bond strength. If it is portion of the element that is toward the applied force, it is on the tested portion of the element. In the figures, these will normally be the parts of the elements that are facing upwards. The directions given of up, down, left, right, above, below etc. are in reference to the orientation of the figures. They are based upon the direction of applied force being vertical from top to bottom of test sample (from the tested end to the untested end).

Reference is now made to FIG. 1. FIG. 1 discloses a general overview of the preferred device embodiment of the invention. The sample preparation device 100 comprises a container 40 and an untested insert 20 and a tested insert 30. On one of the container 40 is an untested insert 20 and on the other is a tested insert 30. Note that the tested insert 30 and untested insert 20 both have protrusions that are inside of the container 40. This will be discussed in more detail shortly.

In the preferred embodiment, the container 40 is a steel pipe and the untested insert 20 and the tested insert 30 are made of a plastic sealant. In alternate embodiments, the container 40 can be made of iron, cored stone, and other cementitious materials (often cement paste/mortar/concrete). In alternate embodiments, the untested insert 20 and the tested insert 30 are made of heat resistant silicone sealant, rubber (i.e. O ring), and semi solid lubricant and other heat resistant sealant products. Choice of the material for the untested insert 20 and the tested insert will be dependent upon the temperature, pressure, desired characteristics, friction, and other desired properties of the test sample 300 (not shown). Note that the materials of the container 40, the untested insert 20, and tested insert 30, can be chosen independent of each other.

It is preferable for the tested insert 30 and the untested insert 20 to be made of a heat resistant material. This will allow for a greater range of temperature experiments. The container 40 is preferably chosen to resemble the material of the casing. It is also possible that the container 40 is made from hollowed stone to test the bond strength between the rock and the outside of a casing. Additionally the inner surface of the container 40 can be adjusted to match the type of pipe on site that is going to be used. For example, the inside of the pipe can be highly polished or rough.

While the cross sectional shape of the container 40 is normally circular or another ellipsoid, this is not a requirement. There are may be situations where a container with another cross section is more effective. For example, in the case where a square foundation was to be filled with a sample material 1, a square cross section may be more appropriate than a circular one.

While the untested insert 20 normally has the same dimensions as the tested insert 30, this is not required. For example, the tested insert 30 can have a larger portion outside of the container 40 in order to provide more stability. Another example is if the protrusions from the untested insert 20 project further into the container so that less test material 1 (not shown) is needed.

The size of the test sample 300 (disclosed in FIG. 3A) produced by the sample preparation device 100 can be adjusted to the desired dimensions by adjusting the dimensions of the container 40. In such a manner, the physical dimensions of a test sample 300 can be adjusted to fit the desired physical dimensions. This can be needed when the test sample 300 is to be placed inside of an existing sample testing system 200 that has a maximum size that can be tested. The size of the container can be adjusted to fit the sample testing system 200 (shown in FIGS. 4-6).

A common size for which testing equipment can accept a test sample 300 with a height of between 25 and 500 mm.

A recommended height is between 1 and 3 times diameter of the test sample, preferably between 1.5 and 2 times diameter, and most preferably 2 times. This is to ensure a proper failure mode (i.e. the load will induce lower bond strength at the interface than the compressive strength of the test sample).

The container 40 could also have an inner diameter of at least five times of the maximum size of the particulate materials within the test sample 300. The minimum size of the inner diameter will also depend upon the material that is being tested. For example, cement paste and cement mortar require a smaller diameter than concrete. Cement paste and cement mortar function best in container sizes that are greater than 20 mm and for concrete greater than 80 mm.

Note that this will depend upon the material that is going to be tested. For example: 30 mm is a common value for cement paste and 300 mm is a common value for concrete. This value is well within the abilities of one skilled in the art Reference is now made to FIG. 2. FIG. 2 discloses a longitudinal exploded perspective cross section of the preferred device embodiment of the invention. The sample preparation device 100 (as mentioned above) comprises a container 40, an untested insert 20 on the untested container end 42, and a tested insert 30 on the tested container end 43. The container 40 has a container inside surface 41.

The untested insert comprises an untested insert body 21. From this untested insert body 21, an untested insert protrusion 22 extends. There is an untested insert surface 23 that is the area on the untested insert body 21 that is encompassed by the untested insert protrusion 22. In a similar manner, the tested insert comprises a tested insert body 31 from which a tested insert protrusion 32 extends. The tested insert surface 33 is the area on the tested insert body 31, which is encompassed by the tested insert protrusion 32. An untested insert gripper 221 is arranged on the untested insert protrusion 22. In a corresponding manner, a tested insert gripper 321 is arranged on the tested insert protrusion 32.

When the sample preparation device 100 is assembled, the untested insert protrusion 22 extends into the container 40 on the untested container end 42 and the tested insert protrusion 32 extend into the container 40 on the tested container end 43. Preferably, all of the outer surface of the untested insert protrusion 22 and the tested insert protrusion 32 make direct contact with the container inside 41. However, it is possible to have a protrusion that has spaces in it such that direct contact is not made along the entire outer surface. The insert protrusions 22,32 aid in minimizing or removing the boundary effects associated with the hardened sample 10 (not shown). The untested insert gripper 221 and the tested insert gripper 321 help keep the untested insert 20 and the tested insert 30 in place inside of the container 40 if needed. Of the two of these, the untested insert gripper 221 may be the more important. There is no gravity to help hold the untested insert 20 in place, as in the case for the tested insert 30.

One skilled in the art would be able to find the appropriate thickness and length of the protrusions 22,32 to minimize boundary effects to an acceptable degree without undue experimentation. The examples presented below of the dimensions can aid one skilled in the art in quickly selecting an appropriate dimensions depending upon the specific application. Please note that minimizing the boundary effects on the tested sample end 13 is more important on the untested sample end 12. This may be due to the fact that the displacement force is applied to the tested sample end 13 during testing. With that in mind, it is possible for the untested insert 20 to not have a untested insert protrusion 22.

Please note that depending on the operational conditions and size of the container 40, the length of the insert protrusions 22,32 may be best expressed as a percentage the container 40 height. In other cases, the length is best expressed as an absolute size.

Another factor that can be important is the relationship between the container 40 height and the diameter of the container 40. Experiments have shown that the height of the container 40 is preferably between 1 and 3 times the diameter of the container 40.

In a preferred embodiment, the tested insert 30 forms a seal that is tight enough to prevent the sample material 1 (not shown) from leaking out of the sample preparation device 100. Leakage is most likely to occur at the tested container end 43.

This seal can be through direct contact between the insert protrusions 22,32 and the container inside 41, or indirect contact where there is an element (such as a gasket) or substance (such as silicon grease) between the insert protrusions 22,32 and the container inside 41.

The grippers' 221,321 main function is to keep the inserts 20,30 in place inside of the container 40 during the process of making a test sample 300. This can be accomplished in several ways. Examples include flexible ribbing or hooks. The grippers 221,321 do not need to extend all around the circumference of the untested insert protrusion 22 and/or the tested insert protrusion 32. These grippers 221,231 can be made of flexible or inflexible material. It can also be threaded to match threads in the untested or tested container end 42,43.

Untested insert body 21 and the tested insert body 31 are shown in the figures as having approximately the same diameter as the outside diameter of the container 40. One advantage of this is that it is easier to place numerous containers 40 in contact together. However, it is also possible for the insert bodies 21,31 to have a larger diameter than the outer diameter of the container. In other words, the insert bodies 21,23 would protrude past the edge of the container. This could be advantageous if a larger top surface of the untested insert 20 and/or the tested insert 30 was needed. The untested insert 20 and the tested insert 30 need not have the same diameter. An increased diameter of the untested insert 20 and/or the tested insert 30 could allow for better clamping around the edges if needed.

In a preferable embodiment, the untested insert surface 23 and the tested insert surface 33 either are even with or enter the container 40. This makes it easier to apply a force along the longitudinal axis of the hardened sample 10 (not shown).

The untested insert surface 23 and the tested insert surface 33 are preferably flat and smooth. The reasons for this will be explained in the discussion of the disclosure of FIG. 3A and FIGS. 4-6.

In an alternate embodiment, there is an element arranged between the untested insert 20 and/or tested insert 30 as disclosed in FIG. 3C. In such a case, the contact between the untested insert protrusion 22 and the tested insert protrusion 32 and the container inside 41 is indirect. It is possible to have one or both of the inserts 22,23 make indirect contact with the container inside 41. This can be chosen independently.

Reference is now made to FIG. 3A. FIG. 3A discloses a longitudinal cross sectional view of the hardened sample 10 formed in the device. The sample material 1 is inserted into the sample preparation device 100 discussed previously. It is preferable that the tested sample end 13 is arranged in an at least partially downwards direction during curing. This improves the quality of the tested surface 131 by ensuring that it is evenly covered in sample material 1 during curing.

The sample material 1 is for example cement paste, cement mortar (with small particle inclusions), and/or concrete (with large particle inclusions), preferably cement paste and/or cement mortar, most preferably cement paste/mortar. This method of preparing a test sample 300 can work on a number of sample materials where testing the bond strength to a container 40 is important.

After the sample material 1 has cured, it forms a hardened sample 10. This hardened sample 10 will be bonded to the container inside 41 (not shown). The shape of the untested insert 20 and the tested insert 30 will shape the hardened sample 10. The test sample 300 (not shown) comprises the hardened sample 10, which begins the test bonded to the container 40 (not shown).

Note that there are dotted lines shown in FIG. 3A. These are to allow an easy visual aid to the location of the untested groove 122 and the tested groove 132.

The hardened sample 10 comprises an untested sample end 12 with an untested surface 121 on one end and a tested sample end 13 with a tested surface 131 on the other end. The tested sample end 13 will have a tested groove 132 around the end, reducing the radius of the tested sample end 13 to less than the container inside 41 (not shown). In a preferable embodiment, the untested sample end 12 will also have an untested groove 122 around the untested sample end 12. The hardened sample 10 also comprises an outer sample surface 11 where the hardened sample is in contact with the container inside 41.

A tested groove 132 will be formed on the tested sample end 13 by the tested insert protrusion 32. The tested groove 132 will have complementary shape to the tested insert protrusion 32. By complementary, it is meant that the depth of the tested groove 132 will be the same as the length of the tested insert protrusion. The shape of the surface of the tested groove 132 will be determined by the inner surface of the tested insert protrusion 32. In a similar manner, the tested surface 131 will have a complementary shape to the tested insert surface 33.

Preferably, the untested sample end will have an untested groove 122 that is shaped complementary to the untested insert protrusion 22 and an untested surface 121 that is complementary to the untested insert surface 23.

In an alternate embodiment, the sample preparation device 100 was not filled entirely with the sample material 1. In this case, the untested groove 122 will be left on the untested sample end 12 that has a complementary shape to the portion of the untested insert protrusion that was within the sample material 1. In a similar matter, the untested surface 121 will be complementary to the portion of the untested insert surface 23 that was in contact with the sample material 1.

It is possible for the length of the protrusions 22,32 to be chosen independently of each other. For example, it may be necessary in a case where boundary effects require deeper grooves 122,132 on one side when compared to another. This may be the case where it is not possible or desirable to fully fill the sample preparation device 100 with sample material 1. In such a case, one of the protrusions would need to be long enough to minimize the boundary effects of the hardened sample 10.

Reference is now made to FIGS. 3B-3D. FIG. 3B discloses a transverse cross sectional view of the preferred embodiment of the sample preparation device 100. As can be seen, the tested insert protrusion 32 is between the edge of the tested sample end 13 and the container 40 on the tested container end 43.

FIG. 3C discloses a transverse cross sectional view of an alternate embodiment of the sample preparation device 100. In this embodiment, there is a sealer 34 between the tested insert protrusion 32 and the container 40. It may be necessary to use a sealer 34 in the event that the seal needs to be improved to prevent the sample material 1 (not shown) from escaping the sample preparation device 100. This sealer 34 can be a physical type such as an o-ring, rubber gasket, calk, and/or wax. Another kind of sealer is of a substance type. For example, a silicone sealant, and/or lubricating grease The important factor is that it improves the seal between the tested insert 30 and the container 40. As in the case of the untested insert protrusion 22 and the tested insert protrusion 32, it is preferable that the sealer 34 is heat resistant over the range of the experimental temperatures.

FIG. 3D discloses a test sample 300 that has been created in the embodiment shown in FIG. 3B after the tested insert 30 has been removed. The tested groove 132 is arranged between the container 40 and the tested sample end 13 where the tested insert 30 was previously located. The tested surface 131 will have the complementary shape to the tested insert surface 33.

Reference is now made to FIGS. 4A and 4B. FIG. 4A discloses an overview of the preferred embodiment of the sample testing system 200. A test sample 300 comprising a hardened sample 10 that is bonded to a container 40 is placed on a support 60. The purpose of the support 60 is to provide support to the test sample 300 when it is under load from a displacement force source 90 (e.g. a hydraulic press). A force applier 50 is in contact with the displacement force source 90 and the test sample 300.

There is an applied force surface 80 on which force is applied to the hardened sample 10. By applied force surface 80 it is meant the surface of whatever element is used to apply force to the tested surface 131. In FIG. 4A, this applied force surface 80 to the hardened sample 10 is the bottom surface of the force applier 50. However, in FIG. 6, the force applier 50 is not in contact with the hardened sample 10, therefore the applied force surface 80 is not the bottom surface of the force applier 50 in FIG. 4A.

FIG. 4B is the same as the sample testing system 200 of FIG. 4A, but with a container insulator 44 around the container 40. The container insulator 44 acts as a thermal insulator or a temperature regulator 44 between the container and the environment around it. This can be quite desirable for studies that look at bond strength as a function of the environmental temperature. It is known that the bond strength can vary with the temperature of cement, pipe walls, and or the surrounding environment. It is not uncommon to cure the sample material 1 inside of a container 40 when forming the test sample 300 at different temperatures by insertion into a heat source (e.g. oven). If the test sample 300 is arranged within the container insulator 44 right after the test sample 300 leaves the oven, it can help to minimize the amount of heat loss during bond strength testing.

Note that this container insulator 44 could also be used during the process of making a test sample 300 itself by arranging the sample preparation device 100 inside of the container insulator 44. This could be desirable for the simulation of the effects on curing temperature to the bonding strength for the test sample 300. It would be possible to use the container insulator 44 both during the making of the test sample 300 and during the testing of the test sample 300 in the sample testing system 200.

The temperature could be regulated by heating the walls of the container itself or by arranging the temperature controller inside of the container insulator. The temperature controller could be, for example, by using electric coils, pipes/tubes that circulate a liquid. This would also allow for the study of environments that are colder or warmer than the laboratory environment Reference is now made to FIG. 5. FIG. 5 discloses a longitudinal exploded perspective cross section of the preferred embodiment of the sample testing system 200. This is a more detailed view of FIG. 4A.

A force applier 50 with a displacement force surface 51 on one end and a force contact surface 52 on the other. The force applier 50 is in contact with the displacement force source 90 at the displacement force surface 51. A test sample 300 comprising a container 40 and a hardened sample 10 is arranged between the force applier 50 and the support 60. It is preferable that the force contact surface 52 is flat. In the preferable embodiment of the fore applier 50 it is shaped as half of a sphere where the force contact surface 52 is directed toward the tested container end 43.

The container is arranged such that the tested container end 43 and the tested sample end 13 is toward the displacement force source 90 and the untested sample end 12 and the untested surface 121 is toward the support 60. The outer sample surface 11 is in contact with the container inside 41. The tested sample end 13 has a tested groove 132 that creates separation between the tested sample end 13 and the container inside 41. The tested surface 131 is shown in contact with the force contact surface 52.

As discussed previously, the applied force surface 80 is the element surface where force is applied to the test sample 300. In this embodiment, this applied force surface 80 is the force contact surface 52 of the force applier 50 that makes contact with the hardened sample 10 at the tested surface 131.

The support 60 comprises a support base 63. A support base groove 61 is arranged on the support base 63. A support base opening 62 is arranged in the support base 63.

The untested container end rests upon the support 60, preferably within the support base groove. The support base opening 62 is there to allow for the hardened sample 10 to be displaced a distance within the container 40 without making contact with the support base 63. This contact will normally be at the untested surface 121.

During operation of the system, the displacement force source 90 applies a downwards force to the force applier 50. The force applier 50 in turn applies force to the tested sample end 13 at the tested surface 131. This applies load to the hardened sample 10. With enough load, the bond between the outer sample surface 11 and the container inside 41 will begin to weaken. This will cause the hardened sample to slide inside of the container 40. There will be a point where the load is sufficient that the bond will break completely and the hardened sample 10 will slide freely. It is important to ensure that this interfacial bond strength is lower than the compressive strength of the hardened sample 10. A support 60 is provided that will prevent the container 40 from moving when force is applied.

When the displacement force source 90 applies load, it is transferred through the force applier 50 and onto the hardened sample 10. Preferably, the force applier 50 has a spherical surface in contact with the displacement force source 90. In the case of a misalignment of the direction of force to the test sample, the spherical contact would allow for the force applier to rotate and allow the force contact surface 52 to remain in proper contact with the tested surface 131.

For best results during this kind of bond strength testing, the force is applied directly along the longitudinal axis of the hardened sample 10. If the force is at an angle, then there may be uneven distribution of force that can possibly change the results to an unacceptable. For example, this could give a lower value of the bond strength because the applied force will induce higher local stresses at the interface between the hardened sample 10 and the container 40. This may induce a premature failure and therefore gives a false value for bond strength. When the displacement force source 90 applies load, it should be applied without shock and increase continuously at a constant rate at the applied force surface 80 until no greater load can be sustained.

In an alternate embodiment, the tested insert 30 can be arranged such that when force is applied the tested insert protrusion 32 will become separated from the tested insert body 31 and be pushed along with the hardened sample 10 during testing. The untested insert body 21 could also be arranged in such a manner. This could be advantageous due to saving time in not having to remove the inserts before. Additionally, this could help support the tested groove 132 and/or the untested groove 122 if needed.

While the support 60 shows a support base 63 with a support base groove 61 arranged to receive the untested container end 42 of the container 40, this support base groove 61 may not necessary. The purpose of this support base groove 61 is at least to increase stability of the container 40 during testing in the case that lateral forces are present. If these forces were not present and/or the container was stable during the testing, then the support base groove 61 could be unneeded.

The purpose of the support base opening 62 is at least to provide an opening for the untested sample end 12 to exit from the container 40 unimpeded. There are other ways to achieve this. One such way is partially filling the sample preparation device 100 with sample material. In such a way, it may be possible to create a test sample 300 where the failure in bond strength would occur while the hardened sample 10 was still within the container 40. Another way to achieve this result is to not to provide support from a support base 63. If clamps were applied to the container 40, it could be held a distance above any motion-impeding surface. It may also be possible to support the test sample from above.

For the best transferal of force, it is best if the force contact surface 52 has a commentary shape to the tested surface 131. In the preferred embodiment, both of these are a flat surface. However, in other embodiments, it may be an advantage if there were protrusions from one surface into the other. This can provide additional stability in some cases.

It is preferable that the shape of the cross section of the applied force surface 80 is the same as the container 40. This helps create an even distribution of force in the event that the applied force surface 80 does not entirely cover the tested surface 131. It is also preferable that the applied force surface 80 is approximately the same size as the container inside 41. This helps to guide the hardened sample 10 evenly through the container 40 because the applied force surface can receive support from the container inside 41.

Reference is now made to FIG. 6. FIG. 6 discloses a longitudinal cross sectional view of an alternative embodiment of the sample testing system 200. In this embodiment, a force adapter 70 is arranged between the force applier 50 and the test sample 300. This force adapter has a force adapter displacement surface 71 that is arranged toward the force contact surface 52. The force adapter also has a force adapter contact surface that is arranged toward the tested surface 131 of the hardened sample 10. In this case the applied force surface 80 is the force adapter contact surface 72 of the force adapter 70.

One reason that a force adapter 70 may be desirable is in the case where a user does not want to change the force applier 50 for different sizes or shapes of containers 1. To reduce the number of components, it may be easier to simply use a force adapter 70 with the desired shapes. It can also be an advantage to have the force applier 50 permanently affixed to the displacement force source 90.

Performing a bond strength test is a multistep process. In the preferable embodiment it is:
1) Making the test sample 300 in the sample preparation device 100:
   a. Inserting an untested insert 20 or a tested insert 30 is inserted into one end of the container 40.
   b. Filling the container 40 with a desired amount with sample material 1.
   c. Placing the other insert 20,30 into the open end of the container 40.
   d. Allowing the sample material 1 is to cure into a hardened sample 10.
   e. Removing the untested insert 20 and the tested insert 30.
2) Running the test
   a. Arranging the test sample 300 into a support such that the container 40 will not move during the testing.
   b. Arranging the force applier 50 between the tested sample end 13 and the displacement force source 90, such that the force contact surface 52 is in contact with the tested surface 131. The force contact surface 52 is considered the applied force surface 80.
   c. Applying a downwards force using a displacement force source 90 and measuring the results until the outer sample surface 11 is no longer bound to the container inside 41.

Note that in making the test sample 300, it also possible to insert both the untested insert 20 and the tested insert 30 and fill the container 40 with sample material 1 through an opening in one of the inserts 20,30. The advantage of this is that it can be easier to get the container completely full. Also, in the preferable embodiment, the test sample is cured with the tested sample end in a downwards position.

Additionally, a force adapter 70 can be inserted between the force applier 50 and the tested sample end 13 such that the force adapter contact surface 72 is in contact with the tested surface 131. In this case, the applied force surface 80 is the force adapter contact surface 72.

In the preferred embodiment, the sample material 1 is added from the untested container end 42 to help reduce the amount of bubbles on the tested sample end 13 of the test sample 300. However, there is nothing that would prevent the addition of sample material 1 from the untested sample end 12. Additionally, it would be possible to add sample material through a hole in the side of the container 40.

In the case where the tested insert 30 and/or the untested insert 20 is not sufficient to remove enough of the boundary effects, it is possible to remove material from the untested sample end 12 or the tested sample end 13. This could be accomplished using a flat bottom drill bit with a radius at least as large as the diameter of the tested sample end. However, the hardened sample 10 should still have a tested groove 132 after the treatment.

It may be desirable to make the test sample 300 in a sample preparation device that is under vacuum. This will help to remove bubbles from the test material 1.

Modifications to the embodiments previously described are possible without departing from the scope of the invention as defined by the accompanying claims. Numerals included within parentheses in the accompanying claims are intended to assist understanding of the claims and should not be construed in any way to limit the subject matter claimed. Reference to the singular is also to be construed as relating to the plural.

We claim:

1. A shear bond strength sample preparation device (100) comprising:
   a container (40) comprising a container inside (41) a tested container end (43) and an untested container end (42);
   an untested insert (20) comprising an untested insert body (21) with an untested insert protrusion (22) extending from the untested insert body (21) wherein an untested insert surface (23) is arranged on the untested insert body (21) between the untested insert body (21) and the untested insert protrusion (22), wherein the untested insert protrusion (22) is annular;
   a tested insert (30) comprising a tested insert body (31) with a tested insert protrusion (32) extending from the tested insert body (31) wherein a tested insert surface (33) is arranged on the tested insert body (31) between the tested insert body (31) and the tested insert protrusion (32), wherein the tested insert protrusion (32) is annular;
   wherein:
   the untested insert (20) is arranged such that the untested insert protrusion (22) is within the container (40) of the untested container end (42);
   the tested insert (30) is arranged such that the tested insert protrusion (32) is within the container (40) on the tested container end (43);
   the untested insert protrusion (22) is arranged on the untested insert body (21) such that the untested insert protrusion (22) is directly or indirectly in contact with the container inside (41); and
   the tested insert protrusion (32) is arranged on the tested insert body (31) such that the tested insert protrusion (32) is directly or indirectly in contact with the container inside (41).

2. The device of claim 1, wherein the tested insert surface (33) is substantially flat.

3. The device according to claim 1, wherein the tested insert protrusion (32) and/or untested insert protrusion extends far enough to remove boundary effects.

4. The device according to claim 3, wherein the container (40) is a pipe.

5. The device according to claim 3, wherein the tested insert protrusion (32) and/or untested insert protrusion extends a distance of between 10 and 30 percent of the height of the container (41).

6. The device of claim 1, wherein the tested insert (30) is arranged such that there is a watertight seal between the tested insert (30) the container inside (41).

7. The device according to claim 6, wherein the sealer (34) consists of one or more of the following: heat resistant silicone sealant, rubber, and semi solid lubricant.

8. The device of claim 1, wherein the tested insert (30) is arranged to shear where the tested body (31) is in contact with the container (40).

9. The device of claim 1, further comprising a sealer (34) to improve waterproofing between the tested insert protrusion (32) and the container inside (41).

10. A method of making a shear bond strength test sample (300) in a shear bond strength sample preparation device (100), the device comprising:
    a container (40) comprising a container inside (41) a tested container end (43) and an untested container end (42);
    an untested insert (20) comprising an untested insert body (21) with an untested insert protrusion (22) extending from the untested insert body (21), wherein the untested insert protrusion (22) is annular;
    a tested insert (30) comprising a tested insert body (31) with a tested insert protrusion (32) extending from the tested insert body (31), wherein the tested insert protrusion (32) is annular;
the method comprising the steps of:
    a) arranging the tested insert (30) into the tested container end (43) of the container (40) such that the tested insert (30) is arranged such that the tested insert protrusion (32) is within the container (40) on the tested container end (43);
    b) providing sample material (1) to the container (40) through the untested container end (42) to a height such that the untested insert protrusion (22) is at least partially covered by performing one of the following steps:
        i. providing a desired amount of sample material (1) to the container (40) and then arranging the untested insert (20) into the untested container end (42) arranged such that the untested insert protrusion (22) is within the container (40) of the untested container end (42); or
        ii. arranging the untested insert (20) into the untested container end (42), such that the untested insert protrusion (22) is within the container (40) of the untested container end (42), and then providing a desired amount of sample material (1) to the container (40) through an opening in the untested insert (20);
    c) arranging the tested container end (43) below the untested container end (42)
    d) waiting until the sample material (1) hardens into a hardened sample (10) bonded to the container inside (41).

11. The method of claim 10, wherein the sample material (1) is one or more of the following: cement paste, cement mortar, and concrete.

12. A shear bond strength sample testing system (200) comprising:
    the shear bond strength test sample (300) of claim 10;
    a support (60) arranged such that the container (40) is held in a fixed position during a test;
    a force applier (50) comprising a force contact surface (52)
    a displacement force source (90);
    wherein:
        the support (60) keeps the container (40) from moving during a test;
            the force contact surface (52) is in at least partial contact with a tested surface (131) at an applied force surface (80); and
        the displacement force source (90) applies a displacement force to the applied force surface (80) in a direction at least partially from the tested container end (43) toward the untested container end (42).

13. The system according to claim 12, wherein the system further comprises a force adapter (70) arranged between the force applier (50) and the hardened sample (10); wherein
    the force adapter (70) comprises an adapter displacement surface (71) on one end a force adapter contact surface (72) on the other; and
    the adapter displacement surface (71) is in at least partial contact with the force contact surface (52) and the adapter contact surface (72) is in at least partial contact with the tested surface (131) at the applied force surface (80).

14. The system according to claim 12, wherein the applied force surface (80) has the same cross sectional shape as the container inside (41), arranged such that it fits inside of the container (10) during testing.

15. The system according claim 12, wherein the force applier (50) shaped as a portion of an ellipsoid.

16. The system according claim 15, wherein the force applier (50) shaped as a half of a sphere.

17. The system according to claim 12, wherein the support (60) is further comprising a support base (63) arranged such that the untested container end (43) rests upon the support base (63).

18. The system according to claim 17, wherein the support (60) is further comprising a base groove (61) and arranged such that the untested container end (43) rests at least partially within the support groove (61).

19. The system according to claim 17, wherein the base support (60) further comprises a support opening (62) arranged such that the hardened sample (10) does not make contact with the support (60), during the test.

20. The system according to claim 19, wherein the support opening (62) is circular and as at least as large as the diameter of the untested sample end (12).

21. The system according to claim 12, further comprising a tested insert (30) arranged to shear where the tested body (31) is in contact with the tested container end (43) upon application of displacement force upon the tested insert (30).

22. A method of testing shear bond strength of a test sample (300) in a shear bond strength testing system (200), wherein the test sample comprises:
    a container (40) comprising a container inside (41) a tested container end (43) and an untested container end (42);
    an untested insert (20) comprising an untested insert body (21) with an untested insert protrusion (22) extending from the untested insert body (21) wherein an untested insert surface (23) is arranged on the untested insert body (21) between the untested insert body (21) and the untested insert protrusion (22);

a tested insert (30) comprising a tested insert body (31) with a tested insert protrusion (32) extending from the tested insert body (31) wherein a tested insert surface (33) is arranged on the tested insert body (31) between the tested insert body (31) and the tested insert protrusion (32);

a hardened sample (10) comprising:
   an untested sample end (12) on the same side of the container as the untested container end (42) on one end of the hardened sample (10) and a tested sample end (13) on the other end of the hardened sample (10), wherein:

the untested insert (20) is arranged such that the untested insert protrusion (22) is within the container (40) of the untested container end (42);

the tested insert (30) is arranged such that the tested insert protrusion (32) is within the container (40) on the tested container end (43):

the untested insert protrusion (22) is arranged on the untested insert body (21) such that the untested insert protrusion (22) is directly or indirectly in contact with the container inside (41); and the tested insert protrusion (32) is arranged on the tested insert body (31) such that the tested insert protrusion (32) is directly or indirectly in contact with the container inside (41)

the untested sample end (12) comprises an untested groove (122) in the hardened sample (10) in contact with the untested insert protrusion (22);

the tested sample end (13) comprises a tested groove (132) in the hardened sample (10) in contact with the tested insert protrusion (32);

wherein the testing system comprises:

a support (60) arranged such that the container (40) is held in a fixed position during testing;

a force applier (50) comprising a force contact surface (52) a displacement force source (90);

wherein:

the support (60) keeps the container (40) from moving during testing;
   the force contact surface (52) is in at least partial contact with a tested surface (131) at an applied force surface (80); and
   the displacement force source (90) applies a displacement force to the applied force surface (80) in a direction at least partially from the tested container end (43) toward the untested container end (42);

the method comprising the steps of:
   a) removing the tested insert (30) and untested insert (20); prior to
   b) arranging the container (40) in the support (60) such that the container is held in place during a test;
   c) arranging the force applier (50) between the displacement force source (90) and the tested sample end (13) such that the force contact surface (52) is in at least partial contact with the tested surface (131); and
   d) applying displacing force upon the hardened sample (10) at the applied force surface (80) between the tested surface (131) and the force contact surface (52); and thereby
   e) causing the hardened sample (10) to displace within the container (40) in the direction of the applied force;
   f) measuring the amount of force applied.

23. The method of claim 22, wherein in step (f):
   a force adapter (70) comprising a force adapter displacement surface (71) is arranged at one end and a force adapter contact surface (72) is arranged at the other;
   the force adapter (70) is arranged between the force applier (50) and the tested sample end (13) such that the force adapter displacement surface (71) is in at least partial contact with the force contact surface (52) and the force adapter contact surface (72) is in at least partial contact with a tested surface (121)

and in step (g):
   the applied force surface (80) is between the tested surface (121) and the force adapter contact surface (72) instead of between force contact surface (52) and the tested surface (121).

24. The method of claim 22, wherein the tested insert protrusion (32) and/or untested insert protrusion (22) extends into the sample material (1) far enough to remove boundary effects.

25. The method according to claim 22, wherein the support (60) is further comprising a support base (63) arranged such that the untested container end (43) rests upon the support base (63) wherein the support (60) is further comprising a base groove (61) and arranged such that the untested container end (43) rests at least partially within the support groove (61).

\* \* \* \* \*